(12) United States Patent
Slazas et al.

(10) Patent No.: US 11,389,311 B2
(45) Date of Patent: Jul. 19, 2022

(54) BRAIDED FLOW DIVERTER USING FLAT-ROUND TECHNOLOGY

(71) Applicant: DEPUY SYNTHES PRODUCTS, INC., Raynham, MA (US)

(72) Inventors: Robert Slazas, Pinecrest, FL (US); Juan A. Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 801 days.

(21) Appl. No.: 14/754,125

(22) Filed: Jun. 29, 2015

(65) Prior Publication Data
US 2015/0297374 A1  Oct. 22, 2015

Related U.S. Application Data

(62) Division of application No. 13/802,225, filed on Mar. 13, 2013, now abandoned.

(51) Int. Cl.
| | | |
|---|---|---|
| *A61F 2/88* | (2006.01) | |
| *D04C 1/06* | (2006.01) | |
| *A61F 2/90* | (2013.01) | |
| *A61B 90/00* | (2016.01) | |
| *A61F 2/82* | (2013.01) | |

(52) U.S. Cl.
CPC .............. *A61F 2/885* (2013.01); *A61B 90/39* (2016.02); *A61F 2/88* (2013.01); *A61F 2/90* (2013.01); *D04C 1/06* (2013.01); *A61B 2090/3966* (2016.02); *A61F 2002/823* (2013.01); *A61F 2230/0006* (2013.01); *A61F 2230/0008* (2013.01); *A61F 2230/0019* (2013.01); *A61F 2250/0028* (2013.01); *A61F 2250/0036* (2013.01); *D10B 2509/06* (2013.01)

(58) Field of Classification Search
CPC .... A61F 2/885; A61F 2/88; A61F 2/90; A61F 2002/823; A61F 2230/0006; A61F 2230/0019; A61F 2230/0008; A61F 2250/0028; A61F 2250/0036; A61B 2090/3966; A61B 90/39; D04C 1/06
See application file for complete search history.

(56) References Cited

U.S. PATENT DOCUMENTS

| | | | |
|---|---|---|---|
| 5,019,057 A | * | 5/1991 | Truckai ............... A61M 25/005 138/123 |
| 5,061,275 A | | 10/1991 | Wallsten |
| 6,361,558 B1 | | 3/2002 | Hieshima |

(Continued)

FOREIGN PATENT DOCUMENTS

| | | |
|---|---|---|
| CN | 101677867 A | 3/2010 |
| CN | 102573701 A | 7/2012 |

(Continued)

*Primary Examiner* — Jennifer Dieterle
*Assistant Examiner* — Rokhaya Diop

(57) ABSTRACT

A generally tubular braided flow diverting stent is formed of alternating round and rectangular elongated members, for treatment of aneurysms. The generally tubular braided flow diverting stent maintains a significant wall thickness while increasing area coverage of a vessel wall. Sliding of the round elongated members over the rectangular elongated members allows the stent to be crimped to very low diameters for delivery in narrow portions of the vasculature.

20 Claims, 1 Drawing Sheet

(56) References Cited

U.S. PATENT DOCUMENTS

| | | | |
|---|---|---|---|
| 7,108,716 B2 * | 9/2006 | Burnside | A61F 2/07 623/1.13 |
| 2002/0179166 A1 | 12/2002 | Houston | |
| 2005/0165470 A1 | 7/2005 | Weber | |
| 2010/0082093 A1 * | 4/2010 | Weber | A61F 2/88 623/1.15 |
| 2012/0150275 A1 | 6/2012 | Shaw-Klein | |

FOREIGN PATENT DOCUMENTS

| | | |
|---|---|---|
| CN | 102727332 A | 10/2012 |
| EP | 2510907 A1 | 10/2012 |
| JP | 2001-509412 A | 7/2001 |
| JP | 2008518681 A | 6/2008 |
| JP | 2012532687 A | 12/2012 |
| WO | WO 2010120926 A1 | 10/2010 |
| WO | WO 2011025887 A1 | 3/2011 |

* cited by examiner

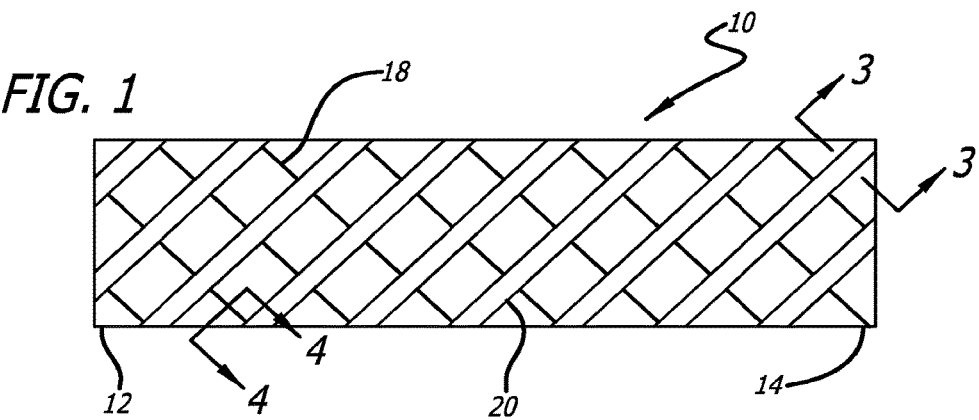
FIG. 1
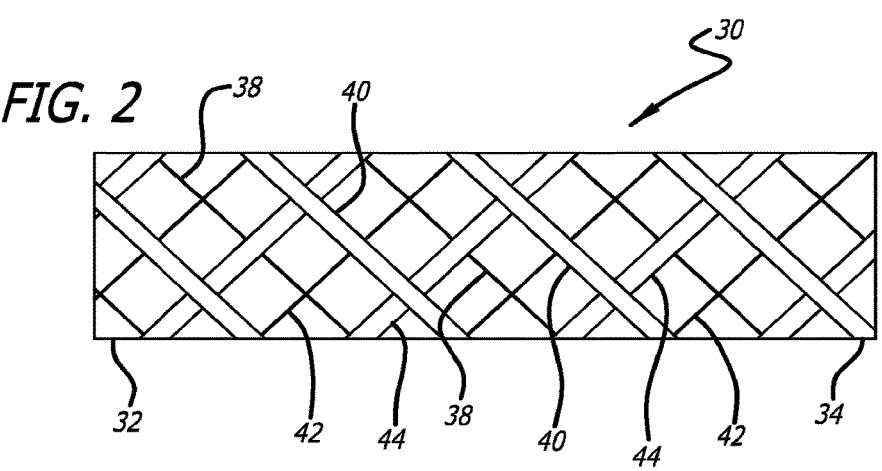
FIG. 2
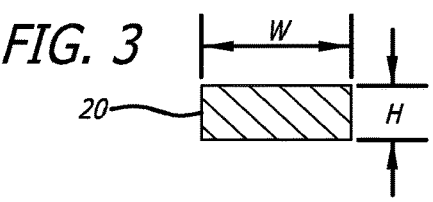
FIG. 3
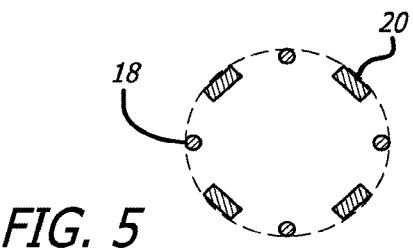
FIG. 4
FIG. 5
FIG. 6

BRAIDED FLOW DIVERTER USING FLAT-ROUND TECHNOLOGY

CROSS REFERENCE TO RELATED APPLICATION

The present application is a divisional of U.S. application Ser. No. 13/802,225 filed Mar. 13, 2013.

BACKGROUND OF THE INVENTION

This invention relates generally to a vascular implant that can be used for treatment of aneurysms, and more particularly concerns a braided flow diverter using flat-round technology to divert flow away from an entrance or neck of an intracranial aneurysm or to define a new luminal flow path through a fusiform aneurysm, as an alternative or supplement to delivery of an embolic coil within such an aneurysm.

Braided stents are typically formed from a plurality of elongate members, such as two or more metal wires, or polymeric fibers or strands of material, for example, and can be very useful in treatment of neurovascular defects. Braided flow diverting stents are commonly constructed from round wires. While the use of round wires in forming such braided flow diverting stents typically provide a maximal wall-thickness for their construction, the amount of vessel area coverage provided by such braided flow diverting stents is not maximized. Braided stents constructed of all rectangular cross-section wires can maximize vessel wall area coverage, but minimize wall thickness. Braided stents made of all rectangular cross-section wires also typically have a more limiting minimum crimped diameter for delivery than a comparable braided flow diverting stent constructed from round wires, since rectangular cross-section wires typically slide less easily past each other than comparable round wires.

It would be desirable to provide a braided flow diverting stent with an improved overall combination of axial flow disruption characteristics, wall coverage and wall thickness, compared to a braided flow diverting stent formed of all rectangular cross-section wires or formed of all round wires. It also would be desirable to provide a braided flow diverting stent that can be crimped to minimum crimped diameters for delivery, comparable to that achievable with braided flow diverting stents constructed from round wires. The present invention meets these and other needs.

SUMMARY OF THE INVENTION

Briefly and in general terms, the present invention provides for a generally tubular braided flow diverting stent formed of alternating round and rectangular elongated members, for treatment of aneurysms. The generally tubular braided flow diverting stent can be utilized to redirect blood flow away from a neck of an intracranial aneurysm, or to define a new luminal flow path through a fusiform aneurysm. The generally tubular braided flow diverting stent maintains a significant wall thickness while increasing area coverage of a vessel wall. The sliding of round elongated members over rectangular elongated members also provides very low crimped diameters to allow delivery of the braided flow diverting stent in narrow portions of the vasculature. Total wall thickness is reduced compared to a braided stent having a similar vessel wall coverage using only round wires. Axial flow disruption is improved compared to a braid of similar vessel wall coverage using only flat wires.

The present invention accordingly provides for a generally tubular braided flow diverting stent for treatment of aneurysms, including one or more first elongate members having a substantially round cross-sectional shape and helically wound in a first helical direction in a generally tubular shape, and one or more second elongate members having a substantially flat radially outer surface and helically wound in a second helical direction counter to the first helical direction and braided with the one or more first elongate members in the generally tubular shape. In a presently preferred aspect, the one or more first elongate members have a substantially circular cross-sectional shape. In another presently preferred aspect, the one or more second elongate members have a cross-sectional thickness in a first direction and a cross-sectional thickness in a second direction perpendicular to the first direction that is substantially greater than the cross-sectional thickness in the first direction. In another presently preferred aspect, the one or more second elongate members have a rectangular cross-sectional shape. In another presently preferred aspect, a plurality of first elongate members are provided, such as a plurality of first wires, for example, and a plurality of second elongate members are provided, such as a plurality of second wires.

In another presently preferred aspect, the one or more first elongate members and the one or more second elongate members may be formed of a material such as stainless steel, nickel-titanium alloy, tantalum, cobalt-chromium alloy, platinum, or combinations thereof. In another presently preferred aspect, at least a portion of the plurality of first elongate members is formed of a bioabsorbable material. In another presently preferred aspect, at least a portion of the plurality of second elongate members comprises a bioabsorbable material. In another presently preferred aspect, at least a portion of the one or more first elongate members and the one or more second elongate members may be formed of a bioabsorbable material such as poly(D,L-lactic acid-co-glycolic acid), polycaprolactone, magnesium, or combinations thereof. In another presently preferred aspect, some of the first and second elongate members optionally may be made of a radio-opaque material to facilitate guidance under imaging methods like fluoroscopy.

In another embodiment, the present invention provides for a generally tubular braided flow diverting stent for treatment of aneurysms, including a plurality of first elongate members having a substantially round cross-sectional shape and helically wound in a first helical direction in a generally tubular shape, a plurality of second elongate members having a substantially flat radially outer surface and helically wound in the first helical direction in the generally tubular shape alternatingly between the plurality of first elongate members, respectively, a plurality of third elongate members having a substantially round cross-sectional shape and helically wound in a second helical direction counter to the first helical direction and braided with the plurality of first elongate members and the plurality of second elongate members in the generally tubular shape, and a plurality of fourth elongate members having a substantially flat radially outer surface and helically wound in a second helical direction counter to the first helical direction and braided with the plurality of first elongate members and the plurality of second elongate members in the generally tubular shape alternatingly between the plurality of third elongate members.

In a presently preferred aspect, the plurality of first elongate members and the plurality of third elongate members each have a substantially circular cross-sectional shape. In another presently preferred aspect, the plurality of second elongate members and the plurality of fourth elongate members each have a cross-sectional thickness in a first direction and a cross-sectional thickness in a second direction perpendicular to the first direction substantially greater than the cross-sectional thickness in the first direction. In another presently preferred aspect, the plurality of second elongate members and the plurality of fourth elongate members each have a rectangular cross-sectional shape.

In another presently preferred aspect, the pluralities of first, second, third and fourth elongate members may be formed of stainless steel, nickel-titanium alloy, tantalum, cobalt-chromium alloy, platinum, or combinations thereof. In another presently preferred aspect, at least a portion of the pluralities of first, second, third and fourth elongate members may be formed of a bioabsorbable material selected from the group consisting of poly(D,L-lactic acid-co-glycolic acid), polycaprolactone, magnesium, or combinations thereof. In another presently preferred aspect, some of the first, second, third and fourth elongate members optionally may be made of a radio-opaque material to facilitate guidance under imaging methods like fluoroscopy.

Other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 1 is a cross-sectional elevational schematic diagram of a first embodiment of a braided flow diverting stent according to the invention.

FIG. 2 is a cross-sectional elevational schematic diagram of a second embodiment of a braided flow diverting stent according to the invention.

FIG. 3 is a cross-sectional view taken along line 3-3 of FIG. 1.

FIG. 4 is a cross-sectional view taken along line 4-4 of FIG. 1.

FIG. 5 is a cross-sectional view taken along line 5-5 of FIG. 1.

FIG. 6 is a cross-sectional view similar to FIG. 5 of an exemplary braided flow diverting stent constructed substantially only from round wires for purposes of comparison.

DETAILED DESCRIPTION OF THE PREFERRED EMBODIMENTS

Referring to the drawings, which are provided by way of example, and not by way of limitation, in a first embodiment, illustrated in FIG. 1, the present invention provides for a generally tubular braided flow diverting stent 10 for treatment of aneurysms, having a proximal end 12, a distal end 14, and an inner lumen (not shown). The generally tubular braided flow diverting stent is preferably formed from a plurality of elongate members, is typically formed from two or more metal wires, or polymeric fibers or strands of material, for example. In a presently preferred aspect, the tubular braided stent optionally may be a self-expanding stent, formed to have a compressed configuration and an expanded configuration. In another presently preferred aspect, the tubular braided stent optionally may be formed of a shape memory material such as a nickel-titanium alloy, for example, having a shape memory position in the expanded configuration. For example, the tubular braided stent may be appropriately heat treated so that the tubular braided stent forms in the desired shape of the expanded shape memory position.

The generally tubular braided flow diverting stent includes one or more first elongate members 18 helically wound in a first helical direction in a generally tubular shape, and one or more second elongate members 20, helically wound in a second helical direction counter to the first helical direction and braided with the one or more first elongate members in the generally tubular shape.

Referring to FIG. 4, the one or more first elongate members preferably have a substantially round cross-sectional shape, such as a substantially circular cross-sectional shape, for example, although the one or more first elongate members may optionally have a substantially oval cross-sectional shape. The one or more first elongate members preferably also are formed of a plurality of first elongate members, such as a plurality of first wires, for example. As is illustrated in FIG. 1, the generally tubular braided flow diverting stent can be formed with round wires wound helically in a right handed helical direction, and rectangular wires wound helically in a left handed helical direction.

Referring to FIG. 3, the one or more second elongate members preferably have a substantially flat radially outer surface. In another presently preferred aspect, the one or more second elongate members typically have a cross-sectional height or thickness H in a first direction and a cross-sectional width or thickness W in a second direction perpendicular to the first direction substantially greater than the cross-sectional height or thickness in the first direction, and typically have a generally rectangular or flattened aspect, for example. The one or more second elongate members preferably also are formed of a plurality of second elongate members, such as a plurality of second wires, for example. The one or more first elongate members and the one or more second elongate members are preferably formed of a material such as stainless steel, nickel-titanium alloy, tantalum, cobalt-chromium alloy, platinum, or the like, or of a polymer, such as a shape memory polymer, or a bioabsorbable material such as poly(D,L-lactic acid-co-glycolic acid) (PGLA), polycaprolactone (PCL), or the like, or combinations thereof. In a presently preferred aspect, some or all of the elongated members used are composed of a bioabsorbable material. In another presently preferred aspect, some or all of the elongate members optionally may be made of a radio-opaque material to facilitate guidance under imaging methods like fluoroscopy.

Referring to FIGS. 5 and 6, the total wall thickness of a generally tubular braided flow diverting stent according to the invention formed utilizing one or more first elongate members having a substantially round cross-sectional shape, and one or more second elongate members having a substantially flat radially outer surface, illustrated in FIG. 5, is reduced compared to a buildup of thickness of the wall of a generally tubular braided flow diverting stent, having a similar vessel wall coverage and formed of all round wires, illustrated in FIG. 6.

In the method of making the generally tubular braided flow diverting stent of the first embodiment, a braider machine can be loaded with bobbins of round wire in all right handed helical locations, and rectangular wire in all left handed helical locations. Conversely, a braider machine can be loaded with bobbins of round wire in all left handed helical locations, and rectangular wire in all right handed helical locations, for example.

In a second embodiment, illustrated in FIG. 2, in which like elements are indicated by like reference numbers, the present invention provides for a generally tubular braided flow diverting stent 30 for treatment of aneurysms. The tubular braided flow diverting stent has a proximal end 32, a distal end 34, and an inner lumen (not shown), and is preferably formed from a plurality of elongate members, typically formed from two or more metal wires, or polymeric fibers or strands of material, for example. In one presently preferred aspect, the tubular braided stent optionally may be a self-expanding stent, formed to have a compressed configuration and an expanded configuration. The tubular braided flow diverting stent can be formed of a shape memory material such as a nickel-titanium alloy, for example, having a shape memory position in the expanded configuration. For example, the tubular braided flow diverting stent may be appropriately heat treated so that the tubular braided flow diverting stent forms in the desired shape of the expanded shape memory position.

The generally tubular braided flow diverting stent of the second embodiment preferably includes a plurality of first elongate members 38 helically wound in a first helical direction in a generally tubular shape, a plurality of second elongate members 40 helically wound in the first helical direction in the generally tubular shape alternatingly between the plurality of first elongate members, a plurality of third elongate members 42 helically wound in a second helical direction counter to the first helical direction and braided with the plurality of first elongate members and the plurality of second elongate members in the generally tubular shape, and a plurality of fourth elongate members 44 helically wound in a second helical direction counter to the first helical direction and braided with the plurality of first elongate members and the plurality of second elongate members in the generally tubular shape alternatingly between the plurality of third elongate members. For example, as is illustrated in FIG. 2, the generally tubular braided flow diverting stent can be formed with alternating round wires and rectangular wires wound helically in both right handed and left handed helical directions.

Referring to FIG. 4, the plurality of first elongate members preferably have a substantially round cross-sectional shape, such as a substantially circular cross-sectional shape, for example, although the one or more first elongate members may optionally have a substantially oval cross-sectional shape, and can be formed by a plurality of first wires, for example.

Referring to FIG. 3, the plurality of second elongate members preferably have a substantially flat radially outer surface. In another presently preferred aspect, the one or more second elongate members typically have a cross-sectional height or thickness H in a first direction and a cross-sectional width or thickness W in a second direction perpendicular to the first direction substantially greater than the cross-sectional height or thickness in the first direction, and typically have a generally rectangular or flattened aspect, and can be formed by a plurality of wires, for example.

Referring to FIG. 4, the plurality of third elongate members preferably have a substantially round cross-sectional shape, such as a substantially circular cross-sectional shape, for example, although the one or more first elongate members may optionally have a substantially oval cross-sectional shape, and can be formed by a plurality of wires, for example.

Referring to FIG. 3, the plurality of fourth elongate members preferably have a substantially flat radially outer surface. In another presently preferred aspect, the one or more fourth elongate members typically have a cross-sectional height or thickness H in a first direction and a cross-sectional width or thickness W in a second direction perpendicular to the first direction substantially greater than the cross-sectional height or thickness in the first direction, and typically have a generally rectangular or flattened aspect, and can be formed by a plurality of wires, for example.

The pluralities of first, second, third and fourth elongate members are preferably formed of a material selected from the group consisting of stainless steel, nickel-titanium alloy, tantalum, cobalt-chromium alloy, platinum, and the like, or of a polymer, such as a shape memory polymer, or a bioabsorbable material such as poly(D,L-lactic acid-co-glycolic acid) (PGLA), polycaprolactone (PCL), or the like, and combinations thereof. In a presently preferred aspect, some or all of the elongated members used are composed of a bioabsorbable material. In another presently preferred aspect, some or all of the elongate members optionally may be made of a radio-opaque material to facilitate guidance under imaging methods like fluoroscopy.

In the method of making the generally tubular braided flow diverting stent of the second embodiment, a braider machine can be loaded with alternating bobbins of round and rectangular wire in both the right handed and left handed helical locations.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A tubular braided flow diverting stent for treatment of aneurysms, comprising:
   a plurality of first elongate members helically wound in a first helical direction in a tubular shape, said plurality of first elongate members having a round cross-sectional shape;
   a plurality of second elongate members helically wound in said first helical direction in said tubular shape alternatingly between said plurality of first elongate members, respectively, said plurality of second elongate members having a flat radially outer surface;
   a plurality of third elongate members helically wound in a second helical direction counter to said first helical direction and braided with said plurality of first elongate members and said plurality of second elongate members in said tubular shape, said plurality of third elongate members having a round cross-sectional shape; and
   a plurality of fourth elongate members helically wound in a second helical direction counter to said first helical direction and braided with said plurality of first elongate members and said plurality of second elongate members in said tubular shape alternatingly between said plurality of third elongate members, said plurality of fourth elongate members having a flat radially outer surface;
   wherein said tubular braided flow diverting stent is a self-expanding stent, said stent having a compressed configuration and an expanded configuration.

2. The tubular braided flow diverting stent of 1, wherein said plurality of first elongate members and said plurality of third elongate members each have a circular cross-sectional shape.

3. The tubular braided flow diverting stent of claim 1, wherein said plurality of second elongate members and said plurality of fourth elongate members each have a cross-sectional thickness in a first direction and a cross-sectional thickness in a second direction perpendicular to said first direction greater than said cross-sectional thickness in said first direction.

4. The tubular braided flow diverting stent of claim 1, wherein said plurality of second elongate members and said plurality of fourth elongate members each have a rectangular cross-sectional shape.

5. The tubular braided flow diverting stent of claim 1, wherein said pluralities of first, second, third and fourth elongate members are formed of a material selected from the group consisting of stainless steel, nickel-titanium alloy, tantalum, cobalt-chromium alloy, platinum, and combinations thereof.

6. The tubular braided flow diverting stent of claim 1, wherein at least a portion of said pluralities of first, second, third and fourth elongate members are formed of a bioabsorbable material selected from the group consisting of poly(D,L-lactic acid-co-glycolic acid), polycaprolactone, magnesium, and combinations thereof.

7. The tubular braided flow diverting stent of claim 1, wherein at least a portion of said pluralities of first, second, third and fourth elongate members are formed of a radio-opaque material.

8. A tubular braided flow diverting stent for treatment of aneurysms, comprising:
    at least one first elongate member helically wound in a first helical direction in a tubular shape, said at least one first elongate member having a round cross-sectional shape; and
    at least one second elongate member helically wound in a second helical direction counter to said first helical direction and braided with said at least one first elongate member in said tubular shape, said at least one second elongate member having a flat radially outer surface;
    at least one third elongate member helically wound in the second helical direction in a tubular shape and braided with said at least one first elongate member in said tubular shape, said at least one third elongate member having a round cross-sectional shape; and
    at least one fourth elongate member helically wound in the first helical direction and braided with said at least one second elongate member in said tubular shape, said at least one fourth elongate member having a flat radially outer surface;
    wherein said tubular braided flow diverting stent is a self-expanding stent, said stent having a compressed configuration and an expanded configuration.

9. The tubular braided flow diverting stent of claim 8, wherein said at least one first elongate member has a circular cross-sectional shape.

10. The tubular braided flow diverting stent of claim 8, wherein said at least one first elongate member comprises a plurality of first elongate members.

11. The tubular braided flow diverting stent of claim 8, wherein said at least one first elongate member comprises a plurality of first wires.

12. The tubular braided flow diverting stent of claim 8, wherein said at least one second elongate member has a cross-sectional thickness in a first direction and a cross-sectional thickness in a second direction perpendicular to said first direction greater than said cross-sectional thickness in said first direction.

13. The tubular braided flow diverting stent of claim 8, wherein said at least one second elongate member has a rectangular cross-sectional shape.

14. The tubular braided flow diverting stent of claim 8, wherein said at least one second elongate member comprises a plurality of second elongate members.

15. The tubular braided flow diverting stent of claim 8, wherein said at least one second elongate member comprises a plurality of second wires.

16. The tubular braided flow diverting stent of claim 8, wherein said at least one first elongate member is formed of a metal, said metal is a material selected from the group consisting of stainless steel, nickel-titanium alloy, tantalum, cobalt-chromium alloy, platinum, and combinations thereof.

17. The tubular braided flow diverting stent of claim 8, wherein said at least one first elongate member is formed of a bioabsorbable material, said bioabsorbable material is selected from the group consisting of poly(D,L-lactic acid-co-glycolic acid), polycaprolactone, magnesium, and combinations thereof.

18. The tubular braided flow diverting stent of claim 8, wherein said at least one first elongate member is formed of a radio-opaque material.

19. The tubular braided flow diverting stent of claim 8, wherein said at least one second elongate member is formed of a radio-opaque material.

20. The tubular braided flow diverting stent of claim 8, wherein one of said at least one first elongate member and said at least one second elongate member being formed of a type of material selected from the group consisting of a metal and a bioabsorbable material, and the other of said at least one first elongate member and said at least one second elongate member being formed of the same type of material.

* * * * *